(12) United States Patent
Yu

(10) Patent No.: US 8,435,240 B2
(45) Date of Patent: May 7, 2013

(54) METAL BONE SUPPORTER FOR NECROSIS OF FEMORAL HEAD

(76) Inventor: Haiying Yu, Beijing (CN)

( * ) Notice: Subject to any disclaimer, the term of this patent is extended or adjusted under 35 U.S.C. 154(b) by 259 days.

(21) Appl. No.: 12/466,665

(22) Filed: May 15, 2009

(65) Prior Publication Data

US 2009/0287214 A1 Nov. 19, 2009

(30) Foreign Application Priority Data

May 16, 2008 (CN) .......................... 2008 1 0111686

(51) Int. Cl.
*A61F 2/28* (2006.01)
*A61B 17/74* (2006.01)

(52) U.S. Cl.
USPC .......................................... 606/65; 623/16.11

(58) Field of Classification Search .............. 606/62–68, 606/95, 301–302, 304–308, 310, 313, 319–320; 433/172–176, 201.1; 623/16.11, 20.34–20.36; 411/383
See application file for complete search history.

(56) References Cited

U.S. PATENT DOCUMENTS

| | | | | |
|---|---|---|---|---|
| 3,852,045 A * | 12/1974 | Wheeler et al. | ............... | 428/566 |
| 4,011,602 A * | 3/1977 | Rybicki et al. | .............. | 623/23.76 |
| 4,259,072 A * | 3/1981 | Hirabayashi et al. | ......... | 433/173 |
| 4,324,550 A * | 4/1982 | Reuther et al. | ................. | 433/174 |
| 4,531,916 A * | 7/1985 | Scantlebury et al. | ......... | 433/173 |
| 4,645,453 A * | 2/1987 | Niznick | .......................... | 433/173 |
| 4,713,003 A * | 12/1987 | Symington et al. | ........... | 433/173 |
| 4,758,160 A * | 7/1988 | Ismail | ............................. | 433/173 |
| 5,145,372 A * | 9/1992 | Daftary et al. | ................. | 433/173 |
| 5,236,431 A * | 8/1993 | Gogolewski et al. | ......... | 606/139 |
| 5,282,746 A * | 2/1994 | Sellers et al. | .................. | 433/172 |
| 5,350,302 A * | 9/1994 | Marlin | ........................... | 433/174 |
| 5,503,558 A * | 4/1996 | Clokie | ........................... | 433/173 |
| 5,611,688 A * | 3/1997 | Hanosh | .......................... | 433/174 |
| 5,755,809 A * | 5/1998 | Cohen et al. | ................ | 623/23.35 |
| 5,759,035 A * | 6/1998 | Ricci | .............................. | 433/174 |
| 5,766,618 A * | 6/1998 | Laurencin et al. | ............. | 424/426 |
| 5,782,918 A * | 7/1998 | Klardie et al. | ................... | 606/60 |
| 5,915,967 A * | 6/1999 | Clokie | ........................... | 433/173 |
| 6,302,913 B1 * | 10/2001 | Ripamonti et al. | ......... | 623/16.11 |
| 6,379,153 B1 * | 4/2002 | Schroering | ..................... | 433/173 |
| 6,537,070 B1 * | 3/2003 | Stucki-McCormick | ....... | 433/174 |
| 6,902,567 B2 * | 6/2005 | Del Medico | ..................... | 606/71 |
| 6,939,135 B2 * | 9/2005 | Sapian | ........................... | 433/174 |
| 7,281,926 B2 * | 10/2007 | Yakir | .............................. | 433/176 |
| 7,300,282 B2 * | 11/2007 | Sapian | ........................... | 433/173 |
| 7,303,396 B2 * | 12/2007 | Abarno | ........................... | 433/173 |
| 8,092,546 B2 * | 1/2012 | Coon et al. | ................. | 623/20.34 |

(Continued)

*Primary Examiner* — Ellen C Hammond
*Assistant Examiner* — Jacqueline Johanas
(74) *Attorney, Agent, or Firm* — Birch, Stewart, Kolasch & Birch, LLP

(57) ABSTRACT

A metal bone supporter for medical bone substitute including a supporter and a connector component which are functionally and structurally designed according to anatomical data and biomechanical data. The titanium alloy powders in the device are able to be scanned, melted and molded through electron beams, to form a cylinder with the strength and elastic modulus similar to cancellous bones of the human body. The supporter component is a porotic spongy body structure with threads on an end, and porous structure forms a rough surface. The connector component is made with a smooth surface and a dense solid mass inside, a thread on an end, and is connected to the supporter component as a removable body. The porous structure enables bone growth, and the device has a high surface friction coefficient, and has a stable structure and mechanical properties are similar to bones.

6 Claims, 3 Drawing Sheets

U.S. PATENT DOCUMENTS

| | | | |
|---|---|---|---|
| 2001/0000486 A1* | 4/2001 | Story | 433/173 |
| 2003/0224328 A1* | 12/2003 | Sapian | 433/173 |
| 2004/0170946 A1* | 9/2004 | Lyren | 433/173 |
| 2005/0014108 A1* | 1/2005 | Wohrle et al. | 433/173 |
| 2005/0112397 A1* | 5/2005 | Rolfe et al. | 428/593 |
| 2005/0244789 A1* | 11/2005 | Crohin et al. | 433/173 |
| 2006/0003179 A1* | 1/2006 | Wang et al. | 428/613 |
| 2006/0136067 A1* | 6/2006 | Pendleton et al. | 623/20.34 |
| 2007/0037123 A1* | 2/2007 | Mansueto et al. | 433/173 |
| 2007/0099152 A1* | 5/2007 | Busch et al. | 433/173 |
| 2007/0148621 A1* | 6/2007 | Yakir | 433/173 |
| 2010/0003640 A1* | 1/2010 | Damstra et al. | 433/201.1 |

* cited by examiner

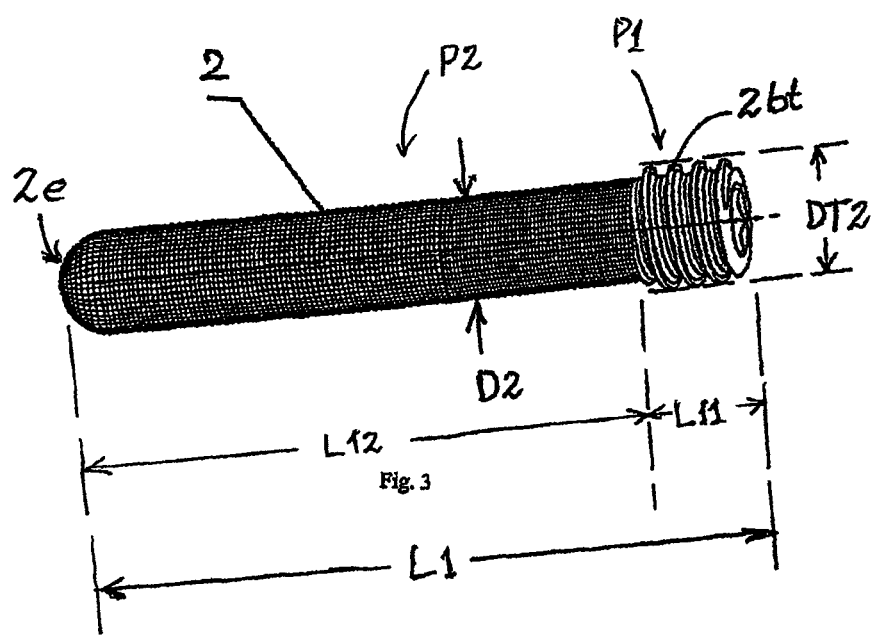

METAL BONE SUPPORTER FOR NECROSIS OF FEMORAL HEAD

CROSS-REFERENCE TO RELATED APPLICATION

The present application claims priority under 35 U.S.C. §119 to Chinese Patent Application No. 2008-10111686.6, filed May 16, 2008, the entire contents of which are hereby incorporated by reference.

BACKGROUND OF THE INVENTION

1. Field of the Invention

The present invention relates to artificial bone material for medical bone transplantation and the preparation of the material, in particular to a metal bone supporter used in the operative therapy of femoral head necrosis for replacing bone grafting to retard the development of the pathological changes.

2. Description of Background Art

It is well-known that autologous bone, allogeneic bone or artificial bone and other substitutes are required to be implanted into the defective part of the bone during the filling, repairing and other orthopedic treatment for all kinds of bone defects in medical orthopedic trauma and the surgical treatment for necrosis for facilitating the bone at the defective part to regain integrity and continuity, so as to achieve the treating purpose of obtaining normal mechanical property. The therapeutic method is called bone transplantation. Bone defect generally presents at joints, wherein, the incidence rate and disability rate of the bone defect caused by necrosis of femoral head are the highest. According to the statistics, the number of the existing patients with femoral head necrosis, which is a common frequently-occurring disease, is more than 8 million in our country. Pathogenic factors of femoral head necrosis are divided into: traumatic necrosis of femoral head, including fracture of the femoral neck, dislocation of hip joint, acetabular fracture and so on; non-traumatic necrosis of femoral head, comprising many primary diseases, metabolic diseases, diseases induced by alcoholic intemperance and hormonal drugs and so on. The analytical data obtained through scanning, calculating and tracing a plurality of patients with femoral head necrosis via MRI indicates that collapse occurs on the patients whose femoral head necrotic area are more than 43%, no collapse appears on the patients whose necrotic area are less than 25%, and the patients whose the necrotic area are between 25% and 43%, are belong to the potential sufferers of collapse. The only effective therapeutic method for the collapse in relation to necrosis of femoral head is artificial hip joint replacement. In order to prevent collapse, early therapeutic methods for necrosis of femoral head include core decompression, bone grafting, stem cell transplantation and other methods, aiming at decreasing the necrotic range, facilitating the bone healing, preventing the collapse of femoral head and retarding the development of pathological changes. Substitute bone for bone grafting comprises biological artificial bone, including autologous bone or allogeneic bone, wherein, autologous bone, which is provided with great regeneration ability, rapid healing and none immune rejection, is the most reliable bone for implantation. However, for the autologous bone is taken from the patient, the source is limited; in addition, because one more operation is required for taking the bone, not only the treatment time is prolonged, but also the suffer of the patient is increased. Although the source of allogeneic bone is abundant, the original mechanical strength of the bone is decreased and various properties are changed after treatment; moreover, allogeneic bone transplantation is possible of causing the transmission of other diseases, lacking security. Both the autologous bone and allogeneic bone transplantation have the disadvantages of long bone ingrowth and creep substitution period, poor mechanical supporting effect and other factors and limited range of operation indication. In recent years, substitute artificial bone, which is made of composite material as tricalcium phosphate, polylactic acid, pearl powder and sodium chloride, has been used in bone transplantation. However, although being close to the performance of the biological bone, the composite artificial bone still has many problems as unstable therapeutic effect, complicated manufacturing process, great cost, insufficient mechanical property and so on. A significant topic in the field is to solve the difficulty in the treatment of patient at the early stage of femoral head necrosis, such as the reduction of necrotic range, facilitation of bone ingrowth and healing, retardation of the development of pathological changes, prevention of collapse caused by necrosis of femoral head, delay or substitution of hip joint replacement and so on. Therefore, the development of bone substitute, which is characterized in effective defect filling capability, fast bone ingrowth, excellent mechanical effect and low cost, becomes a hot job in the field.

SUMMARY OF THE INVENTION

The present invention aims to provide a metal bone supporter and the preparation technique thereof. The supporter, which is able to give sufficient spaces for bone ingrowth and the cell structure, is characterized in good biocompatibility, high skin friction coefficient and steady structure, and is similar to the human bone with regard to the mechanical property. The supporter is capable of providing structural support for the necrotic part of the femoral head since the early stage after implantation, and allowing the bone ingrowth, so as to slower the collapse speed of the femoral head necrotic part, accelerate bone healing, and postpone or prevent the need for the hip joint replacement operation.

In order to achieve the object, a metal supporter used, which comprises a supporter component and a connector component, is designed in the present invention for medical bone replacement by using the technical solution below. The present invention is characterized in that: the supporter component, which is similar to the human cancellous bone in the aspects of the form, intensity and elastic modulus, is a cylinder made of titanium alloy powders by scanning, melting and molding via an electron beam melting fabrication device; the supporter component surface is a porotic spongy body structure, the axis part is solid, a coarse external surface is formed by a porous structure, the pore diameter is 100-800 micron, and the porosity is 50-80%. The connector component, made by mechanical processing, has a smooth external surface and a compact and solid interior. One end of the connector component is provided with a fixing thread. The supporter component and the connector component are in combined connection forming a whole metal bone supporter after connection.

Mechanism and design of the combined connection between the supporter component and the connector component are characterized in that: (1) thread connection between the internal thread and the external thread by direct rotating connection; (2) a fixing bolt is inserted through the center of the supporter component and the connector component for thread connection; (3) based on the operational requirement, the supporter component is used independently. The external surface of one end of the supporter component for independent application is provided with a fixing thread; (4) both the supporter component and the connector component is able to be processed into any other shapes or variant shapes in accordance with the requirements, so as to meet different demands in operation.

The processing steps for preparing the metal bone supporter are as follows:

a. Carry out the engineering design of function and structure for every component of the metal bone supporter according to anatomical data and biomechanical data;

b. Input the information data of the designed supporter component to the computer of an electron beam melting fabrication device, and then carry out layering scanning, high temperature melting, and accumulation for molding;

c. Other parts are molded by mechanical treatment according to the design drawings and parameters;

d. Each component is sterilized separately as per the process requirements, and sealed and packed for standby.

Wherein, the electron beam fusing temperature range in Process Step b is 1800 to 2600° C.

The present invention carries out the functional and structural engineering design for each part of the metal bone supporter based on the anatomy data and the biomechanics data, and then lays the design data of the supporter's supporting component in the electron beam melting fabrication device for forming manufacturing. The operating principle of the forming equipment is: the high-energy electron beam eradiated by the vacuum state electron gun, scans on the evenly laying titanium alloy powder coating in the working chamber after going through the focusing coil and deflecting coil under the control of a computer according to the drawing and data for producing a high temperature of higher than 1800° C. in the target position, so that the metal powders is melted and accumulated by layers for shaping. The remaining parts of the supporter are able to be easily completed by mechanical processing according to the engineering drawings and technical materials. The components are connected by threaded coupling or bolting, so as to finally form the complete metal bone supporter product.

With the electron beam melting fabrication device, the metal bone supporter component is made directly from the titanium alloy powders. Thus, the produce time for designing and processing complex implant is reduced. The energy utilization ratio is high and the processing speed is high, reducing the preparation period from the design to the product and ensuring the consistency of the product. The present invention is characterized in that structure and form of the titanium alloy implant are able to be controlled. It is easy to manufacture both the dense implant component and the implant component with different porosities and similar to the cancellous bone as required by the designer. In addition, different density and porosity are able to be realized in different positions of the same implant simultaneously according to clinical requirements, which is good for steady combination of the implant and the human bone. The supporter component of the metal bone supporter has a porosity between 50% and 80%, and its external surface is rough surface with porous structure with high frictional coefficient, enabling bone ingrowth in the pores after implantation for realization of biological fixation, and improvement of the implantation steadiness, meanwhile having the filling function for bone defects and the structural supporting function. Fixation of the fixing thread on the supporting body or the connector can play instant stabilization and support functions after implantation. The connector is an auxiliary component of the metal bone supporter for accurate positioning and implanting the supporting body to the proper location. The connector is provided with compact and solid interior and smooth external surface. Under specific operation conditions, independent application of the supporter component without the connector component is also allowed if required. Human implantation of the present invention belongs to minimally invasive operation, is able to be completed with local anesthesia and clairvoyance. Therefore the suffering of the patient is reduced, the wound healing is fastened, and the recovery after operation is speeded up.

For adopting the electron beam fusing preparation process, the metal bone supporter has a high skin friction coefficient, a steady structure, and a mechanical property similar to the mechanical property of the human cancellous bone for immediate stabilization and support after implantation, making up the mechanical function defects of bone grafting and other methods in the early stage. Meanwhile, the implant is similar to the human cancellous bone in form and structure, being propitious to the bone ingrowth and the better stabilization in the long term, reducing the collapse speed of the femoral head necrosis, and postponing or preventing the demand for the hip joint replacement operation, so as to achieve the invention objective.

BRIEF DESCRIPTION OF THE DRAWINGS

FIG. 3 is the schematic diagram of a third embodiment of the invention showing independent application of the supporter component.

DETAILED DESCRIPTION OF PREFERRED EMBODIMENTS

Figure 1:
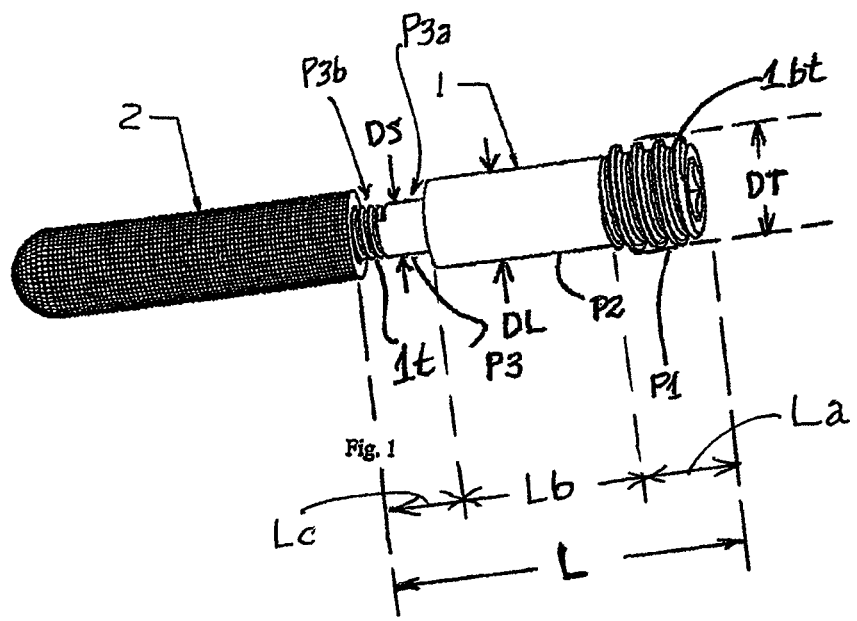
FIG. 1 is the schematic diagram of a first embodiment of the invention showing a direct threaded connection between the supporter component and connector component.
Figure 2:
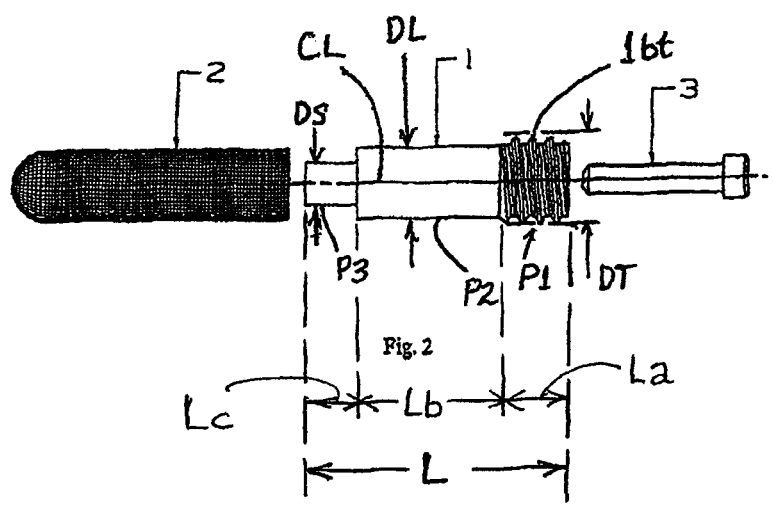
FIG. 2 is the schematic diagram of a second embodiment of the invention in which a fixing bolt is provided for connecting the supporter component to the connector component.

Details of the invention according to the attached drawing:

As shown in FIG. 1, FIG. 2 and FIG. 3, each of the three embodiments of the invention relates to a metal bone supporter for medical bone substitute. The first and second embodiments shown in FIG. 1 and FIG. 2 have a supporter component 2 and a connector component 1. On the other hand, the third embodiment shown in FIG. 3 has a supporter component 2 without the separate connector component 1 of the embodiments shown in FIGS. 1 and 2. The supporter component 2 is a cylinder made of titanium alloy powder by scanning, melting and molding with an electron beam melting fabrication device, and has the strength and elastic modulus similar to cancellous bones of human body; the supporter component 2 is a porotic spongy body structure, of which an axle part is able to be made into solid and the a rough surface is formed by the porous structure. The pore diameter is 100-800 micron, the porosity is 50-80%, the length of supporter component is 20-100 mm and the diameter is 5-15 mm. The connector component 1 used in the first and second embodiments shown in FIGS. 1 and 2 is made through mechanical treatment, with smooth surface and dense solid mass inside. The length of the connector component 1 is 20-100 mm and the diameter DL of portion P2 of the connector component 1 is 5-15 mm. The connector component 1 is provided with a continuous cortical bone thread 1*bt* having a diameter DT which is larger than diameter DL. The supporter component 2 is assembled and integrated with the connector component 1 as a metal bone supporter body. FIG. 1 shows the first embodiment of a thread connecting structure made through direct thread connection of the supporter component 2 and the connector component 1. An internal thread (not shown) is arranged in a flat head end of the supporter component 2. As seen in FIG. 1, the connector component has a length L, is solid from one longitudinal end to the opposite longitudinal end along the central axis CL thereof, and consists of three portions along the length L thereof, each of which has a different outer diameter. The three portions including a first portion P1 (having a length La) at the one longitudinal end of the connector component 1, the first portion P1 having a continuous spiral-shaped cortical bone thread 1bt having an outer diameter DT extending continuously along an entire length La thereof, a second portion P2 (having a length Lb) directly joined to the first portion P1, the second portion P2 having a smooth, cylindrical-shaped outer surface with an outer diameter DL along an entire length Lb thereof, and a third portion P3 at the opposite longitudinal end of the connector component 1 so as to be joinable with the supporter component 2. The third portion P3 (having a length Lc), which is directly joined to the second portion P2, has an outer diameter DS along an entire length thereof, an outer surface of the third portion P3 having two sections, which include a first section P3a directly joining the second portion P2, the outer surface of the first section P3a having a smooth, cylindrical-shape, and a second section P3b directly joining the first section P3a, the outer surface of the second section P3b including a small-diameter fixing thread 1t. The first and second sections P3a, P3b of the third portion P3 of the connector component 1 are able to be fitted into the supporter component 2 in order to connect the supporter component 2 to the connector component 1 to compose the metal bone supporter body. The diameter DT, the diameter DL and the diameter DS have relationships of DT>DL>DS, and La+Lb+Lc=L. FIG. 2 shows the second embodiment in which the connecting structure of the supporter component 2 and the connector component 1 connected is by means of a fixing bolt 3. The fixing bolt 3 is inserted through the center (along a central axis CL) of the supporter component 2 and the connector component 1. A connecting hole (not shown) is arranged in a flat head end of the supporter component 2, and an internal thread (not shown) matching with the fixing bolt 3 is disposed inside the connecting hole of the supporter component 2. As seen in FIG. 2, the connector component 1 has a length L, is hollow from one longitudinal end to the other longitudinal end along the central axis CL thereof, and consists of three portions along the length L thereof, each of which has a different outer diameter. The three portions include a first portion P1 (having a length La) at the one longitudinal end of the connector component, the first portion P1 having a continuous spiral-shaped cortical bone thread 1bt having an outer diameter DT extending continuously along an entire length La thereof, a second portion P2 (having a length Lb) directly joined to the first portion P1, the second portion P2 having a smooth, cylindrical-shaped outer surface with an outer diameter DL along an entire length Lb thereof, and a third portion P3 (having a length Lc) at the opposite longitudinal end of the connector component 1 so as to be joinable with the supporter component 1. The third portion P3 has an outer diameter DS along an entire length Lc thereof, an outer surface of the third portion having a smooth, cylindrical-shape. The third portion P3 of the connector component 1 is able to be fitted into the supporter component 2 in order to connect the supporter component 2 to the connector component 1 to compose the metal bone supporter body. As in Embodiment 1, the diameter (DT), the diameter (DL) and the diameter (DS) of Embodiment 2 have relationships of DT>DL>DS, and La+Lb+Lc=L. The connector component 1 has a hollow structure having central axis CL, and an end of the fixing bolt 3 passes along the central axis CL, through the connector component 1, and then is inserted into the connecting hole of the supporter component 2. Then, the fixing bolt 3 is connected with the internal thread inside the connecting hole of the supporter component 2, forming a metal bone supporter body. As in the first embodiment shown in FIG. 1, the non-connecting end of the second embodiment shown in FIG. 2 is also provided with a continuous cortical bone thread 1bt having a diameter DT which is larger than diameter DL. In each of the embodiments shown in FIGS. 1 and 2, the continuous cortical bone thread 1bt extends continuously around the smooth, cylindrical-shaped outer surface of the portion P1. FIG. 3 shows the third embodiment of the supporter component 2 for independent use in the metal bone supporter. When the supporter component 2 is in use independently, an external fixation common thread 2bt (or a continuous cortical bone thread 2bt) is arranged on the flat head end of the supporter component 2, to fix the supporter component 2 of the metal bone supporter at the required position on bones of the human body. In practical application, the shape of the metal bone supporter can be processed to any other or variant shapes as required.

As can be understood from FIG. 3, the supporter component 2 of the metal bone supporter is able to be used independently without being assembled with the connector component 1. As can be seen in FIG. 3, supporter component 2 consists of two portions along the length L1 thereof, each of which has a different outer diameter. The two portions include a first portion P1 (having a length L11) at one longitudinal end of the supporter component 1, the first portion P1 having a continuous spiral-shaped cortical bone thread 2bt having an outer diameter DT2 extending continuously along an entire length L11 thereof; and a second portion P2 (having a length L12) directly adjoining the first portion P1 and extending from the first portion P1 to the opposite longitudinal end of the supporter component 1. The second portion P2 having a cylindrical-shaped outer body with an outer diameter D2 along the length L12 of the second portion, except for at the one rounded end 2e of the second portion P2 where the outer diameter decreases. The outer diameter DT2 of the first portion P1, and the outer diameter D2 of the second portion P2 have a relationship of DT2>D2. In addition the total length L1 of the supporter component 2, the length L11 of the first portion, and the length L12 of the second portion have relationships of L12>L11, and L12+L11=L1.

Processing steps for preparing the metal bone supporter:

a. Carry out the engineering design of function and structure for every component of the metal bone supporter according to anatomical data and biomechanical data;

b. Input the information data of the designed supporter component to the computer of an electron beam melting fabrication device, and then carry out layering scanning, high temperature melting, and accumulation for molding;

c. Other parts are molded by mechanical treatment according to the design drawings and parameters;

d. Each component is sterilized separately as per the process requirements, and sealed and packed for standby.

I claim:

1. A metal bone supporter for treating the femoral head necrosis comprising:
   a supporter component and a connector component having a common central axis (CL) when assembled together to compose a metal bone supporter body,
   wherein the supporter component is a cylinder that is made of titanium alloy powder,
   the supporter component has a rough outer surface having a porous structure, wherein a diameter of pores of the porous structure is 100-800 micrometers, and the porosity is 50-80%;
wherein the connector component has a length (L), is solid from one longitudinal end to the opposite longitudinal end along the central axis (CL) thereof, and consists of three portions along the length (L) thereof, each of which has a different outer diameter, the three portions being:
a first portion at the one longitudinal end of the connector component, the first portion having a continuous spiral-shaped cortical bone thread (1*bt*) having an outer diameter (DT) extending continuously along an entire length (La) of the first portion of the connector component;
a second portion directly joined to the first portion, the second portion having a smooth, cylindrical-shaped outer surface with an outer diameter (DL) along an entire length (Lb) thereof,
a third portion at the opposite longitudinal end of the connector component so as to be joinable with the supporter component, the third portion directly joined to the second portion and the third portion having an outer diameter (DS) along an entire length (Lc) thereof, an outer surface of the third portion having two sections:
a first section directly joining the second portion, the outer surface of the first section having a smooth, cylindrical-shape, and
a second section directly joining the first section, the outer surface of the second section including a small-diameter fixing thread (1*t*),
the first and second sections of the third portion of the connector component being fitted into the supporter component in order to connect the supporter component to the connector component to compose the metal bone supporter body,
wherein the diameter (DT), the diameter (DL) and the diameter (DS) have relationships of:
DT>DL>DS, and
La+Lb+Lc=L.

2. The metal bone supporter of claim 1 for treating the femoral head necrosis, wherein the supporter component is assembled and integrated with the connector component by directly connecting an internal thread of the supporter component with the small-diameter fixing thread (1*t*) on the third portion of the connector component.

3. The metal bone supporter of claim 1, for treating the femoral head necrosis, by scanning, wherein the supporter component is made of molded titanium alloy powder by melting and molding with an electron beam melting fabrication device.

4. A metal bone supporter for treating the femoral head necrosis, comprising:
a supporter component and a connector component having a common central axis (CL) when assembled together to compose a metal bone supporter body,
wherein the supporter component is a cylinder that is made of titanium alloy powder,
the supporter component has a rough, cylindrical-shaped outer surface having a porous structure,
wherein a diameter of pores of the porous structure is 100-800 micrometers, and the porosity is 50-80%;
wherein the connector component has a length (L), is hollow from one longitudinal end to the other longitudinal end along the central axis (CL) thereof, and consists of three portions along the length (L) thereof, each of which has a different outer diameter, the three portions being:
a first portion at the one longitudinal end of the connector component, the first portion having a continuous spiral-shaped cortical bone thread (1*bt*) having an outer diameter (DT) extending continuously along an entire length (La) of the first portion of the connector component;
a second portion directly joined to the first portion, the second portion having a smooth, cylindrical-shaped outer surface with an outer diameter (DL) along an entire length (Lb) thereof,
a third portion at the opposite longitudinal end of the connector component so as to be joinable with the supporter component, the third portion directly joined to the second portion and the third portion having an outer diameter (DS) along an entire length (Lc) thereof, an outer surface of the third portion having a smooth, cylindrical-shape,
wherein the third portion of the connector component being fitted into the supporter portion in order to connect the supporter component to the connector component to compose the metal bone supporter body,
wherein the diameter (DT), the diameter (DL) and the diameter (DS) have relationships of:
DT>DL>DS, and
La+Lb+Lc=L,
the metal bone supporter further comprising:
a fixing bolt which extends along the common central axis (CL) through the hollow connector component and makes a connection with the supporter component, thereby assembling together the support component and the connector component to compose the metal bone supporter body.

5. A metal bone supporter for treating the femoral head necrosis comprising:
a solid supporter component having a total length (L1), having one end with a continuous cortical bone thread (2*bt*), and an opposite end having a cylindrical-shape body with one rounded end (2*e*),
the supporter component is made of titanium alloy powder, and an entire outer surface, except for the one end having the continuous cortical bone thread (2*bt*), is provided with a rough porous structure,
wherein a diameter of pores of the porous structure is 100-800 micrometers, and the porosity is 50-80%,
wherein the supporter component consists of two portions along the length (L1) thereof, each of which has a different outer diameter, the two portions being:
a first portion at one longitudinal end of the supporter component, the first portion having a continuous spiral-shaped cortical bone thread (2*bt*) having an outer diameter (DT2) extending continuously along an entire length (L11) of the first portion;
a second portion having a length (L12), directly adjoining the first portion, and extending from the first portion to the opposite longitudinal end of the supporter component,
the second portion having the cylindrical-shaped outer body with an outer diameter (D2) extending continuously along the length (L12) of the second portion, except for the one rounded end (2*e*) where the outer diameter (D2) decreases,
wherein the outer diameter (DT2) and the outer diameter (D2) have a relationship of DT 2>D2, and
the length (L1), the length (L11) and the length (L12) have the relationships of:
L12>L11, and
L12+L11=L1.

6. The metal bone supporter of claim 5, for treating the femoral head necrosis, by scanning, wherein the supporter component is made of molded titanium alloy powder by melting and molding with an electron beam melting fabrication device.

* * * * *